US009538726B2

(12) United States Patent
Komatsubara et al.

(10) Patent No.: US 9,538,726 B2
(45) Date of Patent: *Jan. 10, 2017

(54) ABSORBENT ARTICLE FOR PETS

(75) Inventors: Daisuke Komatsubara, Kanonji (JP); Takeshi Ikegami, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 73 days.

This patent is subject to a terminal disclaimer.

(21) Appl. No.: 14/126,401

(22) PCT Filed: Apr. 26, 2012

(86) PCT No.: PCT/JP2012/061286
§ 371 (c)(1),
(2), (4) Date: Dec. 13, 2013

(87) PCT Pub. No.: WO2012/172874
PCT Pub. Date: Dec. 20, 2012

(65) Prior Publication Data
US 2014/0290589 A1 Oct. 2, 2014

(30) Foreign Application Priority Data
Jun. 14, 2011 (JP) .................. 2011-132547

(51) Int. Cl.
*A01K 23/00* (2006.01)
*A61F 13/15* (2006.01)

(52) U.S. Cl.
CPC ...... *A01K 23/00* (2013.01); *A61F 2013/15186* (2013.01)

(58) Field of Classification Search
CPC .... A01K 13/006; A01K 23/00; A01K 23/005; A61F 2013/15186; A61F 13/5622; A61F 13/62

(Continued)

(56) References Cited

U.S. PATENT DOCUMENTS 4,770,298 A * 9/1988 McFarland ........... A61F 5/4401
206/390
4,966,286 A * 10/1990 Muckenfuhs ...... B65D 75/5833
206/440

(Continued)

FOREIGN PATENT DOCUMENTS

JP 2004-159592 A 6/2004
JP 2007-020533 A 2/2007

(Continued)

OTHER PUBLICATIONS

Extended European Search Report dated Nov. 9, 2015, corresponding to European Patent Application No. 12800935.4.

(Continued)

*Primary Examiner* — Monica Williams
(74) *Attorney, Agent, or Firm* — Hauptman Ham, LLP

(57) ABSTRACT

An absorbent article for pets includes a top sheet, a back surface layer, an absorbent core, a first end portion, a second end portion, and a pair of side portions. Such absorbent articles for pets are stacked and packaged while each absorbent article is folded and the portion of the back surface layer which is near the first end portion forms a first outer surface. The absorbent article for pets also includes: a hook member provided on the portion of the back surface layer which is near the first end portion; an engaging section provided on the portion of the top sheet which is near the second end portion and engageable with the hook member; and a weak engagement section provided at a position at which the weak engagement section is in contact with the hook member of an adjacent absorbent article of the stacked absorbent articles for pets.

4 Claims, 14 Drawing Sheets

(58) Field of Classification Search
USPC ........ 119/869, 867, 868, 850, 856; 604/358,
604/385.01, 385.11, 385.201, 385.23,
385.24, 604/386, 387, 389, 391
See application file for complete search history.

(56) References Cited

U.S. PATENT DOCUMENTS

| | | | |
|---|---|---|---|
| 5,275,588 A * | 1/1994 | Matsumoto | A61F 13/58 604/358 |
| 6,710,221 B1 * | 3/2004 | Pierce | A61F 13/42 604/361 |
| 2003/0069555 A1 * | 4/2003 | Erdman | A61F 13/49011 604/369 |
| 2006/0074390 A1 | 4/2006 | Price et al. | |
| 2007/0129702 A1 | 6/2007 | Gribben | |
| 2010/0094235 A1 * | 4/2010 | Solomon | A01K 23/00 604/359 |
| 2010/0312207 A1 * | 12/2010 | Rezai | A61F 13/5622 604/365 |
| 2011/0209675 A1 * | 9/2011 | Esperon | A61D 9/00 119/868 |

FOREIGN PATENT DOCUMENTS

| | | |
|---|---|---|
| JP | 2007-190178 A | 8/2007 |
| JP | 2009-254278 A | 11/2009 |
| WO | 2004/007316 A1 | 1/2004 |

OTHER PUBLICATIONS

Office Action mailed Aug. 18, 2015, corresponding to Japanese patent application No. 2011-132547.

* cited by examiner

ABSORBENT ARTICLE FOR PETS

RELATED APPLICATIONS

The present application is a National Phase of Application Number PCT/JP2012/061286, filed Apr. 26, 2012, which claims priority to Japanese Application Number 2011-132547 filed Jun. 14, 2011.

TECHNICAL FIELD

The present invention relates to an absorbent article for pets.

BACKGROUND ART

Disposable diapers for pets such as cats and dogs have been proposed. Such disposable diapers for pets, when worn by a pet, capture the pet's urine and feces by covering the anus and urethral opening located between the bases of hind legs of the pet.

Depending on the type of pet (for example, miniature dachshund having a long body and short legs), the urethral opening can locate forward of the area between the bases of the hind legs. Also, the urethral opening of a male dog is positioned farther forward compared to a female dog. When a disposable diaper for pets is worn by such a pet, whose urethral opening is positioned forward of the area between the bases of its hind legs, there have been cases where the urethral opening is exposed from the diaper, resulting in urine leakage.

Thus, an absorbent article for pets, configured in a rectangular shape to be wrapped around the waist of a pet, has been proposed (for example, see Patent Document 1).

With such absorbent article for pets configured in a rectangular shape, the urethral opening is reliably covered when worn by pet regardless of its position.

[Patent Document 1] Japanese Unexamined Patent Application, Publication No. 2007-20533

DISCLOSURE OF THE INVENTION

Problems to be Solved by the Invention

An absorbent article for pets to be used wrapped around the waist of a pet, as proposed in Patent Document 1, is, for example, worn by a pet in the following procedures.

Firstly, a user positions one longitudinal end of an absorbent article for pets on the back of a pet, and holds it down with one hand in the vicinity of the one longitudinal end. Secondly, while holding the one longitudinal end by the hand, the user holds the other end of the absorptive article for pets and pulls it to wrap it around and cover the belly of the pet with the absorbent article for pets. Following this, the user pulls the other end of the absorbent article for pets so that the side sections along the longitudinal direction of the absorptive article for pets come in close contact with the waist of the pet and, in this state, the user engages the inner face of the other end of the absorbent article for pets with the outer face of the one end. Consequently, the absorbent article for pets remains wrapped around the waist of the pet in a preferred manner.

The above mentioned absorbent article for pets having a rectangular shape is packaged in a bag on the production line, in which an assembled plurality thereof is packaged with each member being longitudinally folded in two or three. Thereafter, the absorbent article for pets is distributed in the form of a package where a plurality thereof is packaged in a bag.

A potential problem with conventional absorbent articles for pets is that during a step where a plurality thereof are packaged into a package, the folded and stacked absorbent articles for pets become displaced from each other and cannot be packaged in a bag stably.

Accordingly, an object of the present invention is to provide an absorbent article for pets, configured so that a stacked plurality thereof are packaged in a bag stably without being easily displaced from each other.

Means for Solving the Problems

The present invention relates to an absorbent article for pets including: a liquid-permeable top sheet; a liquid-impermeable back surface layer; and an absorbent core sandwiched between the top sheet and the back surface layer. The absorbent article for pets is configured in a rectangular shape having: a first end portion and a second end portion opposite each other; and a pair of side portions opposite each other and perpendicular to the first end portion and the second end portion. The absorbent article for pets is packaged as a stacked plurality of the absorbent article for pets, in which each absorbent article for pets of the stacked plurality thereof being folded and a first outer face is formed by a back surface layer side in a vicinity of the first end portion. The absorbent article for pets includes: a hook member disposed on the back surface layer side in the vicinity of the first end portion; an engaging section disposed on a top sheet side in a vicinity of the second end portion and engageable with the hook member; and a weak engagement section disposed at a position that comes into contact with the hook member of an adjacent absorbent article for pets in a stacked state, allowing the hook member to engage with a weaker force than an engagement force for the engaging section.

Furthermore, preferably, the absorbent article for pets is longitudinally folded in two and a second outer face is formed by the back surface layer side in the vicinity of the second end portion. A plurality of the absorbent articles for pets is stacked in a configuration where the first outer face of one of the plurality of the absorbent articles for pets abuts against the second outer face of an absorbent article for pets that is disposed adjacent to the one of the plurality of the absorbent articles for pets. The weak engagement section is provided in the second outer face.

Furthermore, preferably, the back surface layer is configured including a nonwoven fabric engageable with the hook member. The weak engagement section is formed by the back surface layer.

Furthermore, preferably, the top sheet is configured including a nonwoven fabric engageable with the hook member. The engaging section is formed by the top sheet.

Effects of the Invention

In accordance with the present invention, an absorbent article for pets ensures stable packaging without being displaced easily from each other when a stacked plurality thereof are packaged in a bag.

EXPLANATION OF REFERENCE NUMERALS

Figure 1:
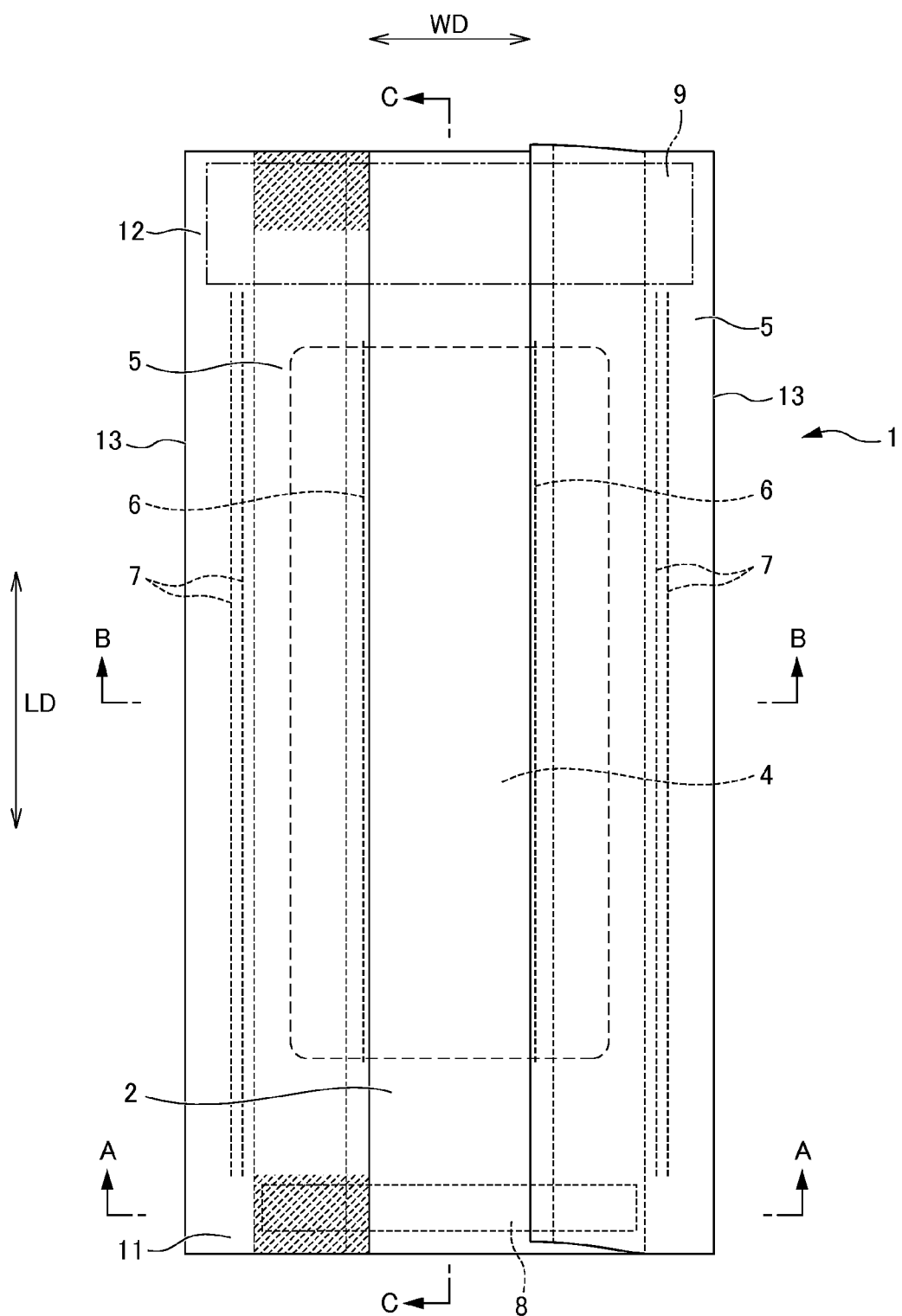
FIG. 1 is a plan view of an absorbent article for pets of a first embodiment viewed from a top sheet side.

1. Absorbent article for pets
2. Top sheet
3. Back surface layer
4. Absorbent Core
8. Hook tape (hook member)
9. Engaging section (loop member)
10. Weak engagement section
11. First end portion
12. Second end portion
14. First outer face
15. Second outer face

EMBODIMENTS FOR CARRYING OUT THE INVENTION

Preferable embodiments of an absorbent article for pets of the present invention will now be described with reference to the drawings.

Firstly, an absorbent article 1 for pets of a first embodiment will be described. The absorptive article 1 for pets of the first embodiment is configured to have a rectangular shape, having a first end portion 11 and a second end portion 12 opposite each other, and a pair of opposing side portions 13 perpendicular to the first end portion 11 and the second end portion 12, as shown in FIG. 1.

Figure 2:
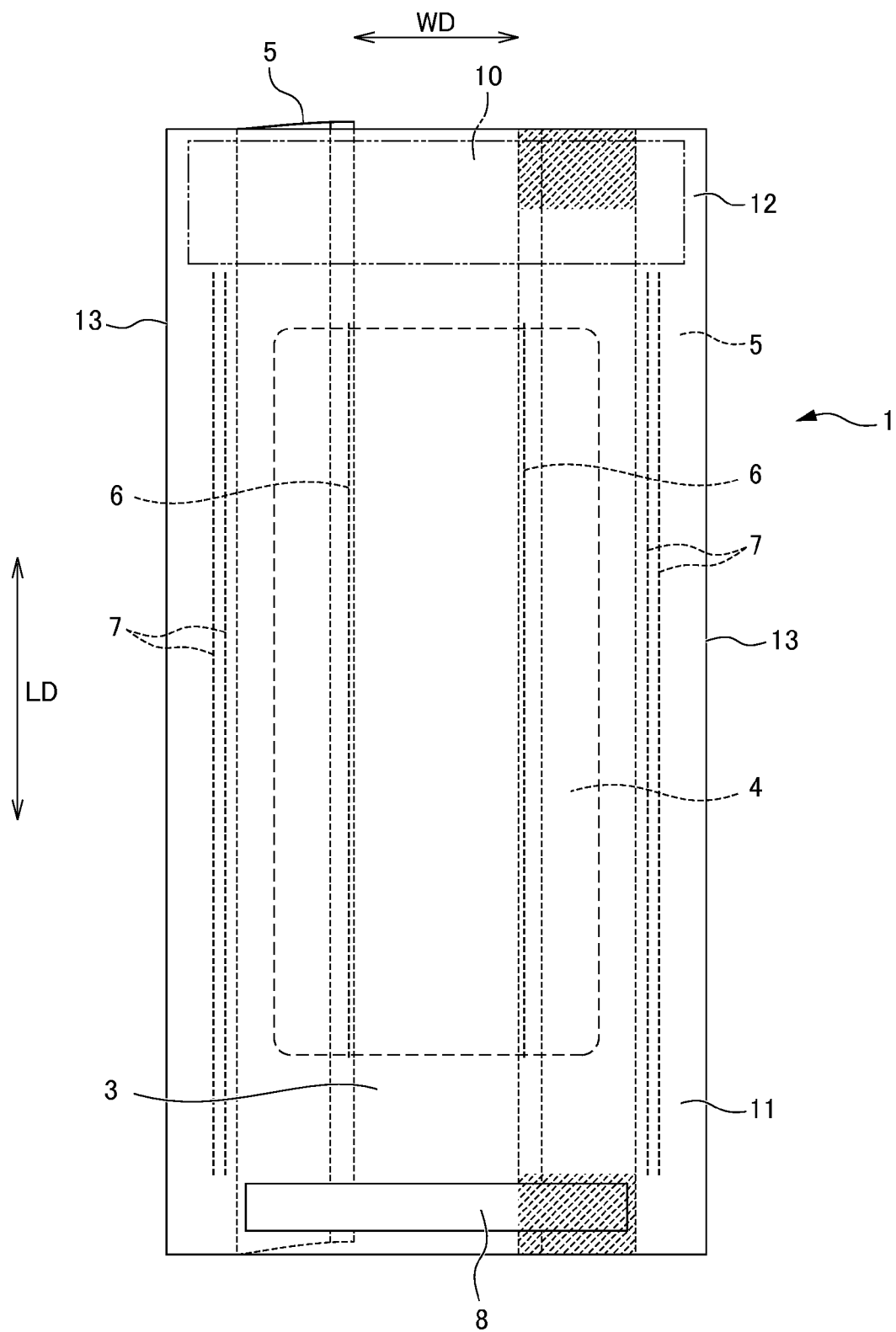
FIG. 2 is a plan view of the absorbent article for pets of the first embodiment viewed from a back surface layer side.

The absorbent article 1 for pets includes, as shown in FIGS. 1 and 2, a liquid-permeable top sheet 2, a liquid-impermeable back surface layer 3, an absorbent core 4, a pair of side sheets 5, 5, a first elastic member 6, a second elastic member 7, a hook tape 8 as a hook member, an engaging section 9, and a weak engagement section 10.

The top sheet 2 primarily forms a face of a side contacting the body of a pet, which is the wearer. The top sheet 2 is made of a porous or non-porous nonwoven fabric, which is engageable with the hook tape 8 mentioned below.

Figure 3:
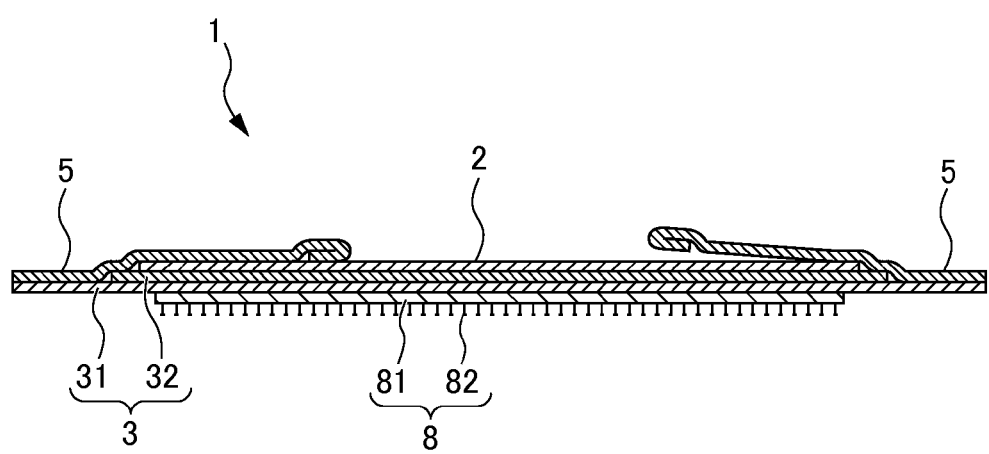
FIG. 3 is a cross-sectional view taken along the A-A line of FIG. 1.
Figure 4:
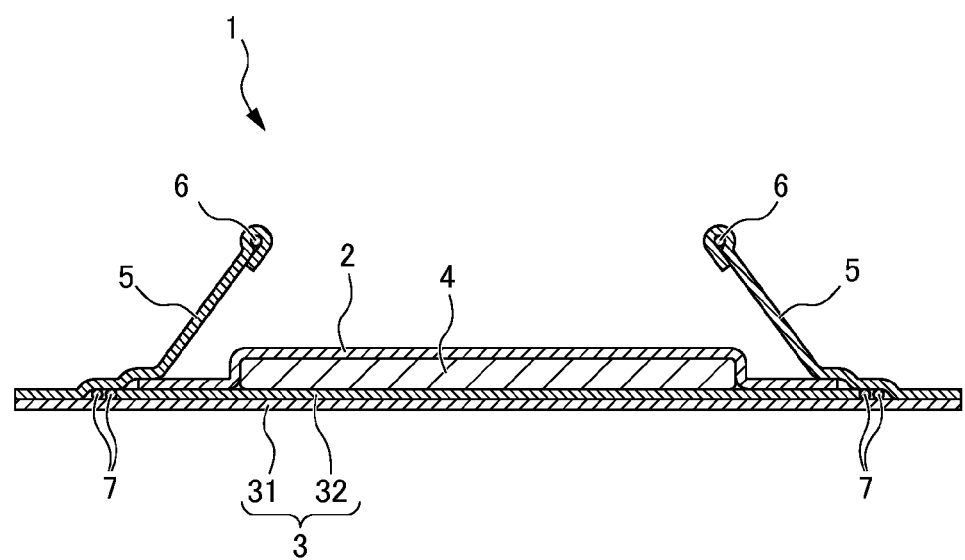
FIG. 4 is a cross-sectional view taken along the B-B line of FIG. 1.
Figure 5:
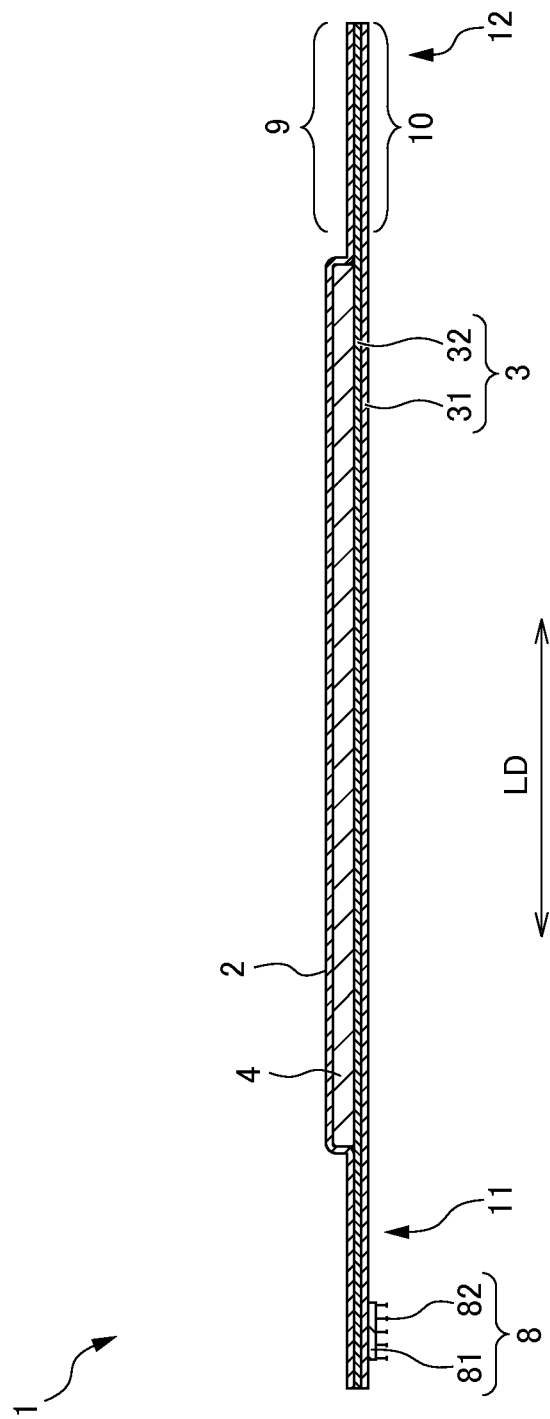
FIG. 5 is cross-sectional view taken along the C-C line of FIG. 1.

The back surface layer 3 includes, as shown in FIGS. 3 to 5, a back surface sheet 31 forming a face of a reverse side of the absorbent article 1 for pets, and a wet-proof sheet 32 disposed on a top sheet 2 side of the back surface sheet 31.

The back surface sheet 31 is made of a nonwoven fabric that is engageable with the hook tape 8. More specifically, a hydrophobic nonwoven fabric, laminated sheet of nonwoven fabric and water-impermeable plastic film, SMS nonwoven fabric in which a highly water-resistant melt-blown nonwoven fabric is sandwiched by durable spun-bond nonwoven fabrics, and the like are useable for the back surface sheet 31.

For the wet-proof sheet 32, in addition to the materials similar to those used for the back surface sheet 31, a water-impermeable plastic film or similar may be used.

In the first embodiment, the back surface sheet 31, although engageable with the hook tape 8, is made of a nonwoven fabric having a weaker engagement force for the hook tape 8 compared to the nonwoven fabric constituting the top sheet 2.

The absorbent core 4 is interposed between the top sheet 2 and the back surface layer 3 layered with each other, as shown in FIGS. 4 and 5. For the absorbent core 4, fluff pulp and superabsorbent polymer, wrapped by a core wrap material such as tissue, may be used.

A pair of side sheets 5, 5 is configured to have a rectangular shape having small width, and individually disposed on either longitudinal side of the top sheet 2 on the side contacting the pet body. Outer edge sides of the pair of side sheets 5, 5 are joined to side portions of the back surface sheet 31. A part of inner edge sides of the pair of side sheets 5, 5 is a free end.

For the side sheets 5, 5, a water-repellent or hydrophobic material is preferably used. Specifically, for the side sheets 5, 5, different nonwoven fabrics such as a spun-lace nonwoven fabric, spun-bond nonwoven fabric, thermal-bond nonwoven fabric, melt-blown nonwoven fabric, needle-punch nonwoven fabric, air-through nonwoven fabric, and the like, may be used. In the first embodiment, the side sheets 5, 5 are made of a nonwoven fabric engageable with the hook tape 8.

The first elastic member 6 is disposed in the vicinity of the inner edge of each member of the pair of side sheets 5, 5. The second elastic member 7 is disposed on each member of the pair of side portions 13 along the longitudinal direction LD of the absorbent article 1 for pets.

For the first elastic member 6 and the second elastic member 7, a natural rubber product such as rubber yarn and flat rubber, or a thermoplastic elastomer such as urethane, ethylene vinyl acetate (EVA) copolymer, and PE, may be used.

The hook tape 8 is disposed on an outer face of the back surface sheet 31 in the vicinity of the first end portion 11 of absorbent article for pets. The hook tape 8 has a belt-like configuration, and is disposed so that its longitudinal direction is in line with the width direction WD of the absorbent article 1 for pets.

The hook tape 8 includes, as shown in FIGS. 3 and 5, a belt-like base portion 81 and a plurality of hook portions 82 disposed on one face of a base 81.

The base portion 81 and a plurality of the hook poritons 82 of the hook tape 8 are integrally formed using a synthetic resin material such as polypropylene or the like.

The engaging section 9 is disposed on a top sheet 2 side in the vicinity of the second end portion 12, as shown in FIGS. 1 and 5. In the first embodiment, the engaging section 9 is configured by the top sheet 2 and the side sheet 5, respectively disposed in the vicinity of the second end portion 12.

The weak engagement section 10, as mentioned below, is disposed at a position that comes in contact with the hook tape 8 of adjacently disposed the absorbent articles 1 for pets when a plurality of absorbent articles 1 for pets is assembled in a state where each member is folded into a predetermined shape (see FIGS. 7 and 8). This weak engagement section 10 has an engagement force that allows the hook tape 8 to engage with a weaker engagement force than an engagement force for the engaging section 9.

In the first embodiment, the weak engagement section 10 is formed by the back surface sheet 31 disposed in the vicinity of the second end section 12, as shown in FIGS. 2 and 5.

Figure 6:
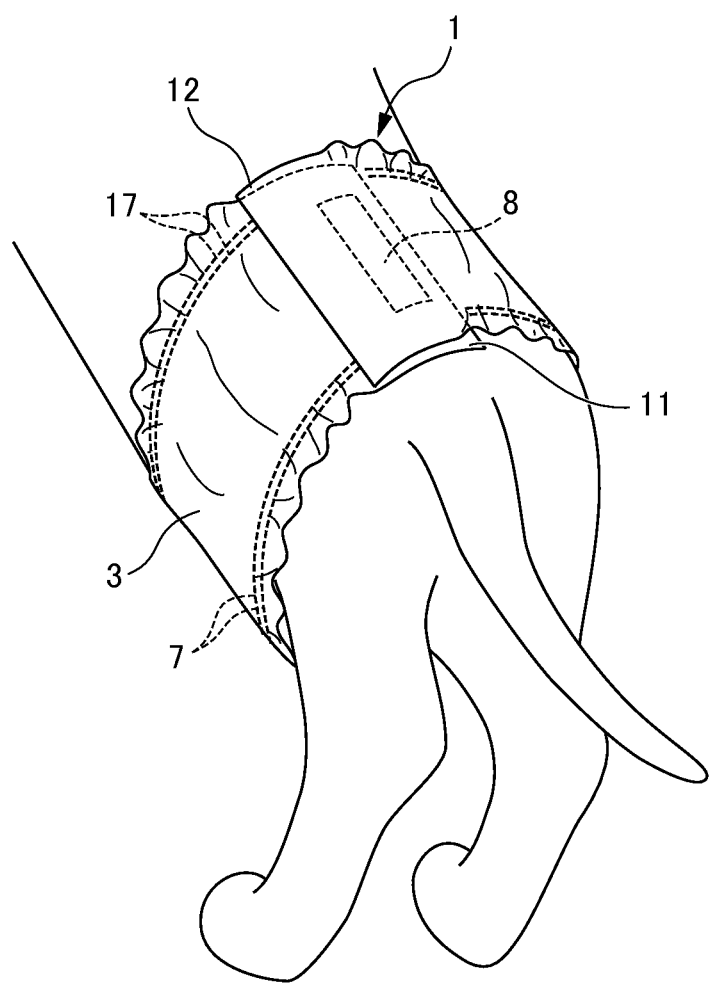
FIG. 6 shows the absorbent article for pets of the first embodiment in a state worn by a pet.

The above mentioned absorbent article 1 for pets is worn around the waist of a pet, as shown in FIG. 6. Specifically, firstly, the first end portion 11 of the absorbent article 1 for pets is positioned on the back of a pet, and in this state while the vicinity of the first end portion 11 is being held down, the second end portion 12 is pulled around to wrap and cover the belly of the pet with the absorbent article 1 for pets. Secondly, the engaging section 9 disposed on the inner face of the second end portion 12 is engaged with the hook tape 8 disposed on the back surface sheet 31 side of the first end portion 11. Consequently, the absorbent article 1 for pets remains wrapped around the waist of the pet.

Figure 7:
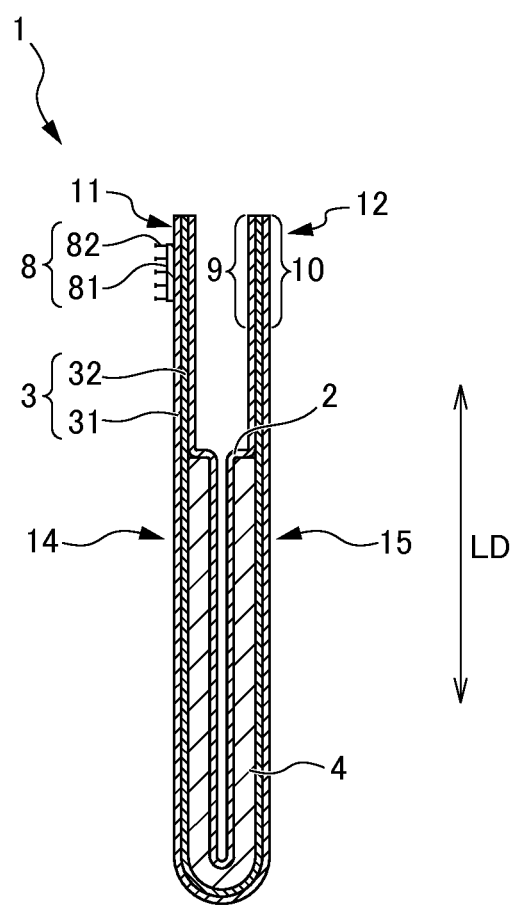
FIG. 7 is a longitudinal cross-sectional view showing the absorbent article for pets in a folded state.
Figure 8:
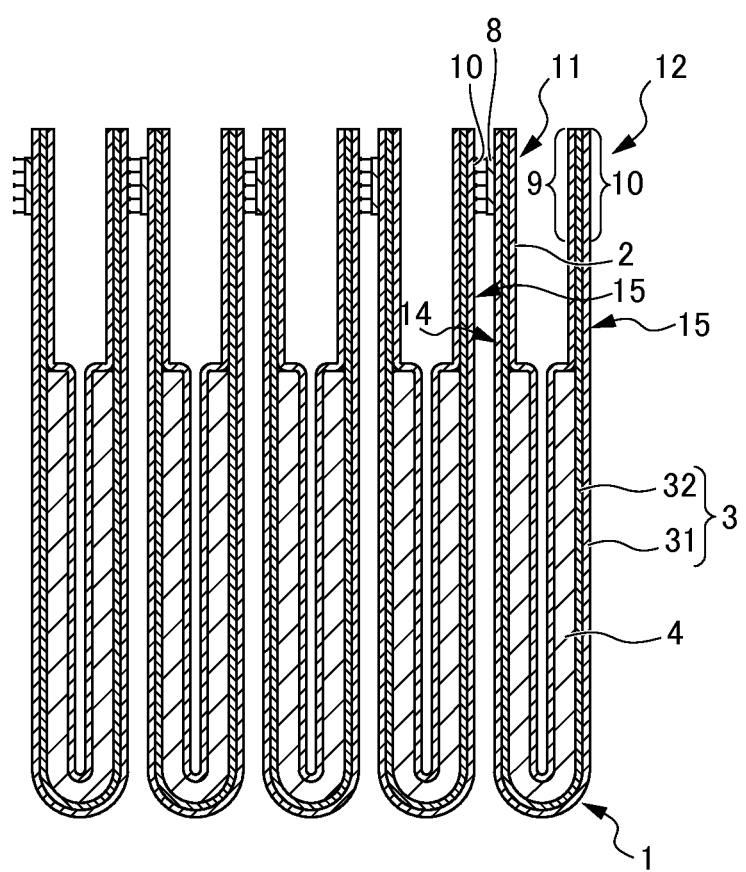
FIG. 8 is a cross-sectional view showing a plurality of absorbent articles for pets in a folded and stacked state.
Figure 9:
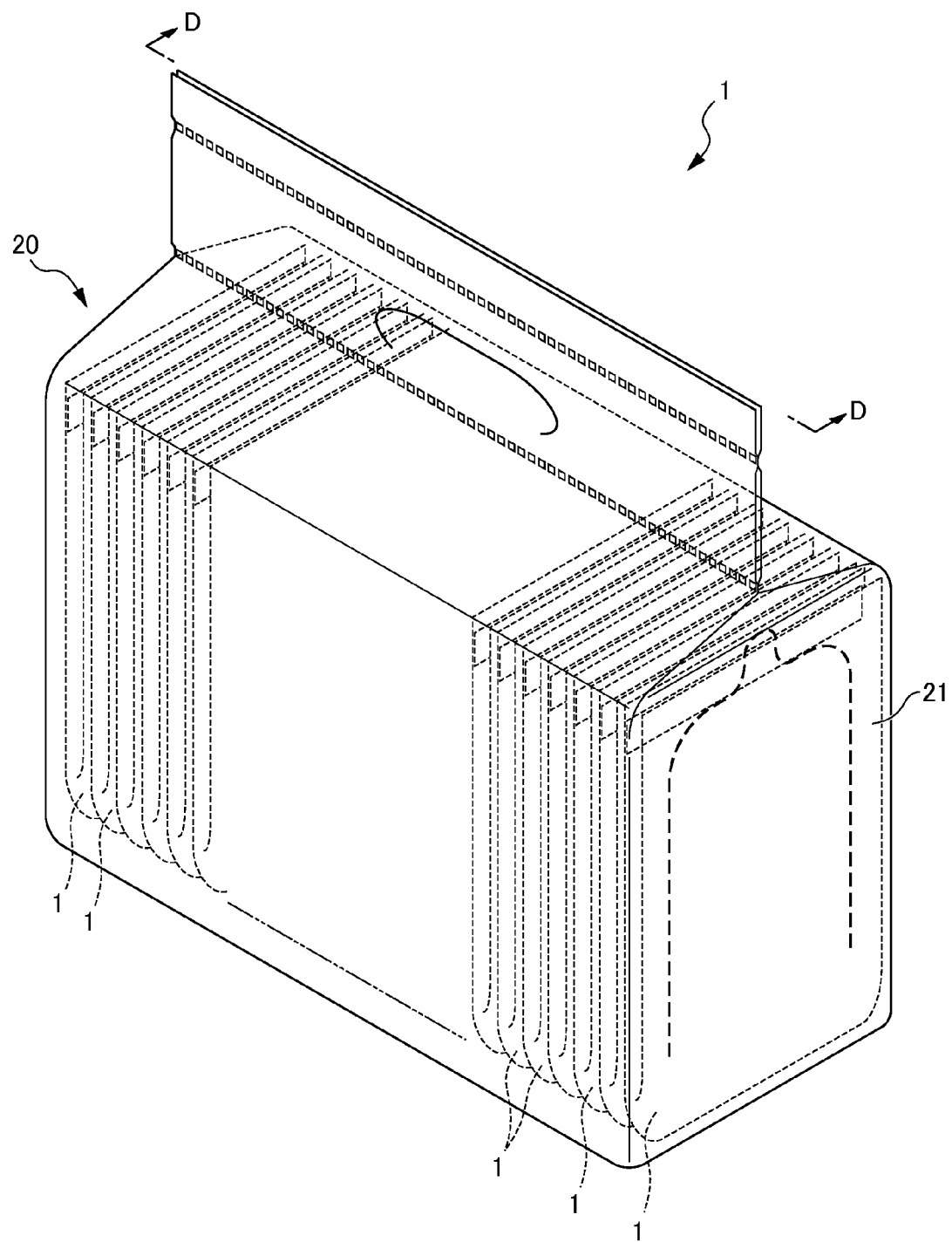
FIG. 9 is a perspective view showing a plurality of absorbent articles for pets in a state where they are folded, stacked, and packaged in a bag.
Figure 10:
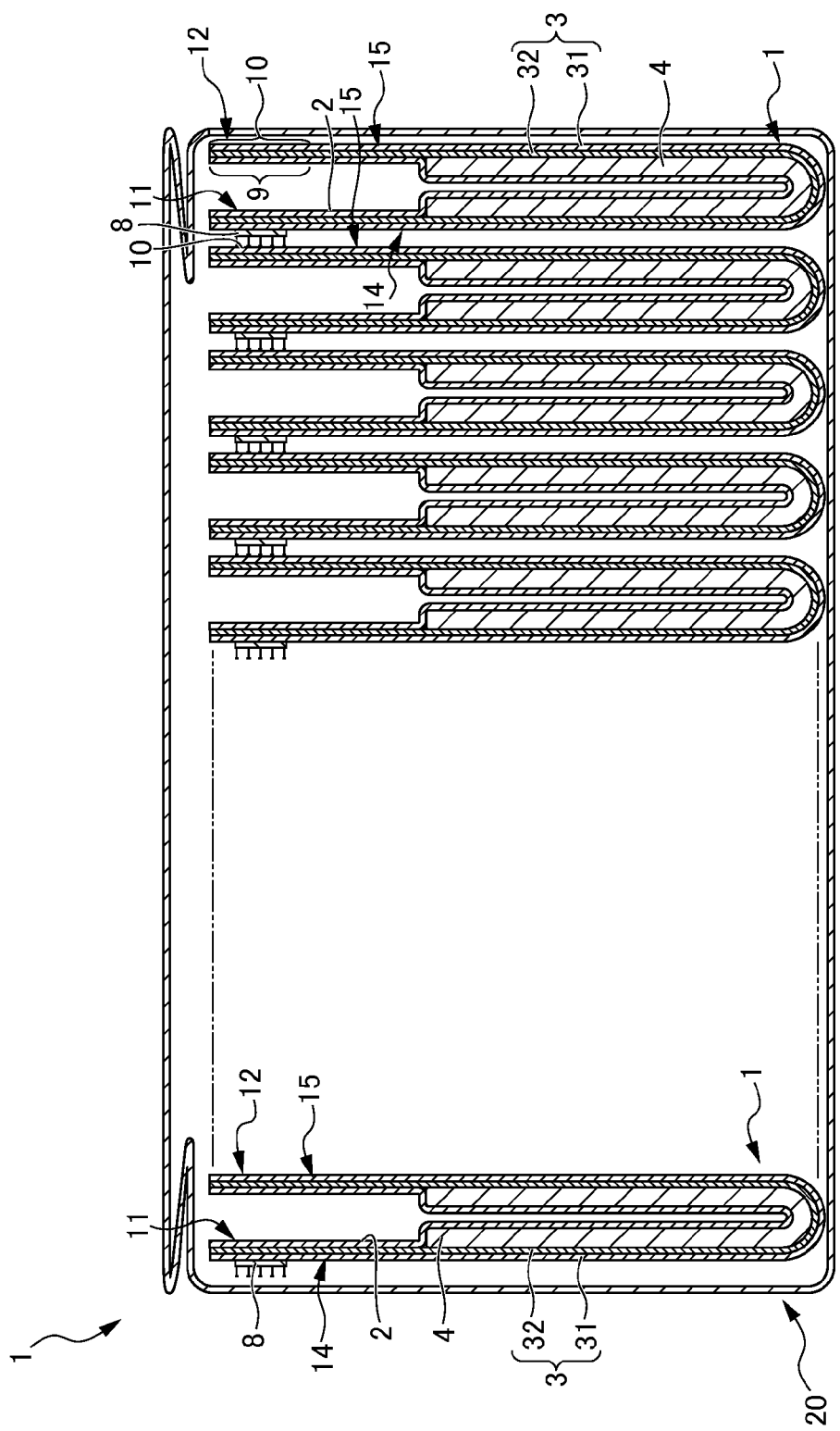
FIG. 10 is a cross-sectional view taken along the D-D line of FIG. 9.

FIG. 7 is a longitudinal cross-sectional view showing the absorbent article 1 for pets in a folded state, and FIG. 8 is a cross-sectional view showing a plurality of the absorbent articles 1 for pets in a folded and stacked state. FIG. 9 is a perspective view showing a plurality of the absorbent articles 1 for pets in a state folded, stacked, and packaged in a bag 20, and FIG. 10 is a cross-sectional view taken along the D-D line of FIG. 9.

The absorbent article 1 for pets of the present invention, as shown in FIGS. 7 to 10, is folded in the longitudinal direction LD on the production line, and then a plurality thereof are stacked together and packaged in the bag 20. Thereafter, the absorbent article 1 for pets is distributed in a state where it is included in a package with a plurality thereof contained in the bag 20.

More specifically, the absorbent article 1 for pets is folded so as to have a first outer face 14 and a second outer face 15, as shown in FIG. 7.

In the first embodiment, the manufactured absorbent article 1 for pets is folded in two in the longitudinal direction LD so that the top sheet 2 faces inside, as shown in FIG. 7. Thus, in the first embodiment, both the first outer face 14 and the second outer face 15 are configured with the back surface sheet 31 mainly.

More specifically, the first outer face 14 is formed with the back surface sheet 31 mainly, which is on a first end portion 11 side in the longitudinal direction LD of the absorbent article 1 for pets. This first outer face 14 is provided with the hook tape 8.

The second outer face 15 is formed with the back surface sheet 31 mainly, which is on a second end portion 12 side in the longitudinal direction LD of the absorbent article 1 for pets. A section in the vicinity of the second end portion 12 of the back surface sheet 31 that configuring the second outer face 15, forms the weak engagement section 10.

A plurality of the absorbent articles 1 for pets in a folded state is stacked so that the first outer face 14 of one absorbent article 1 for pets abuts against the second outer face 15 of the absorbent article 1 for pets disposed adjacent to the one absorbent article 1 for pets, as shown in FIG. 8. Consequently, the hook tape 8 of the one absorbent article 1 for pets abuts against the vicinity of the second end portion 12 in the second outer face 15 of the adjacently disposed the absorbent article 1 for pets. Here, the second outer face 15 of the absorbent article 1 for pets has been provided with the weak engagement section 10. Therefore, the stacked and folded plurality of the absorbent articles 1 for pets is weakly fastened with each other, or with adjacent the absorbent article 1 for pets, by the engagement of the hook tape 8 and the weak engagement section 10.

A stacked plurality of the absorbent articles 1 for pets is packaged in the bag 20, as shown in FIGS. 9 and 10. Here, the plurality of the absorbent articles 1 for pets has been stacked in a state where they are weakly fastened to each other. Consequently, the stacked plurality of the absorbent articles 1 for pets is not easily displaced from each other when they are packaged in the bag 20.

In accordance with the absorbent article 1 for pets of the first embodiment described above, the following operational effects are obtained.

(1) The absorbent article 1 for pets is folded in the longitudinal direction LD on the production line, and a plurality thereof is stacked and packed in the bag 20 to be packaged. Thus, the absorptive article 1 for pets was configured to include: the hook tape 8 disposed on a the back surface sheet 31 side of the first end portion 11; and the engaging section 9 disposed on the top sheet 2 side of the second end portion 12. Furthermore, the weak engagement section 10 was disposed at a position that comes in contact with the hook tape 8 of the absorbent article 1 for pets adjacently disposed in a stacked state. Consequently, when the absorbent article 1 for pets is worn around the waist of a pet, the hook tape 8 disposed on the first end portion 11 is engaged with the engaging section 9 disposed on the second end portion 12, thereby facilitating putting the absorbent article 1 for pets around the waist of the pet. Also, folding the absorbent article 1 for pets in a way that the first outer face 14 is formed by the back surface sheet 31 side in the vicinity of the first end portion 11, enables engagement of the hook tape 8 and the weak engagement section 10 of adjacently disposed the absorbent articles 1 for pets in a state where a plurality of folded absorbent articles 1 for pets is stacked. Thus, the hook tape 8 for putting the absorbent article 1 for pets on a pet can also be used for weakly fastening a plurality of absorbent articles 1 for pets as an assembly, preventing displacement of the plurality of the absorbent articles 1 for pets from each other, thereby enabling stable packaging of the stacked plurality of the absorbent articles 1 for pets in the bag 20.

Because the stacked plurality of the absorbent articles 1 for pets is not displaced from each other, the back surface sheet 31 is less likely to get scratches in rubbing against abutting the hook tape 8. Thus, in a step for packaging the absorbent article 1 for pets in the bag 20, damage on the absorbent article 1 for pets can be reduced.

(2) Along with the folding of the absorbent article 1 for pets so that the second outer face 15 is formed by the back surface sheet 31 side of the second end section 12, this second outer face 15 was provided with the weak engagement section 10. Thus, the weak engagement section 10 can be disposed on the back surface sheet 31 side. Hence, prior to use of the absorbent article 1 for pets, the hook tape 8 will not engage with the top sheet 2 side which will contact the body of a pet; therefore, the stacked plurality of the absorbent articles 1 for pets can be securely packaged in the bag 20 without causing damage on the top sheet 2 side prior to use of the absorptive article 1 for pets.

(3) The back surface sheet 31 was configured including nonwoven fabric that was engageable with the hook tape 8, and the weak engagement section 10 was formed by the back surface sheet 31. Consequently, the stacked plurality of the absorbent articles 1 for pets can be weakly fastened without a need for attaching additional members, thus enabling reduction of production cost for the absorbent article 1 for pets.

(4) The top sheet 2 and the side sheets 5, 5 were configured including a nonwoven fabric allowing the hook tape 8 to engage therewith, and the engaging section 9 was formed by the top sheet 2 and the side sheets 5, 5. This enables engagement of the first end portion 11 and the second end portion 12 without a need for attaching additional members to the top sheet 2 side of the second end portion 12, thus enabling reduction of production cost for the absorbent article 1 for pets.

Figure 11:
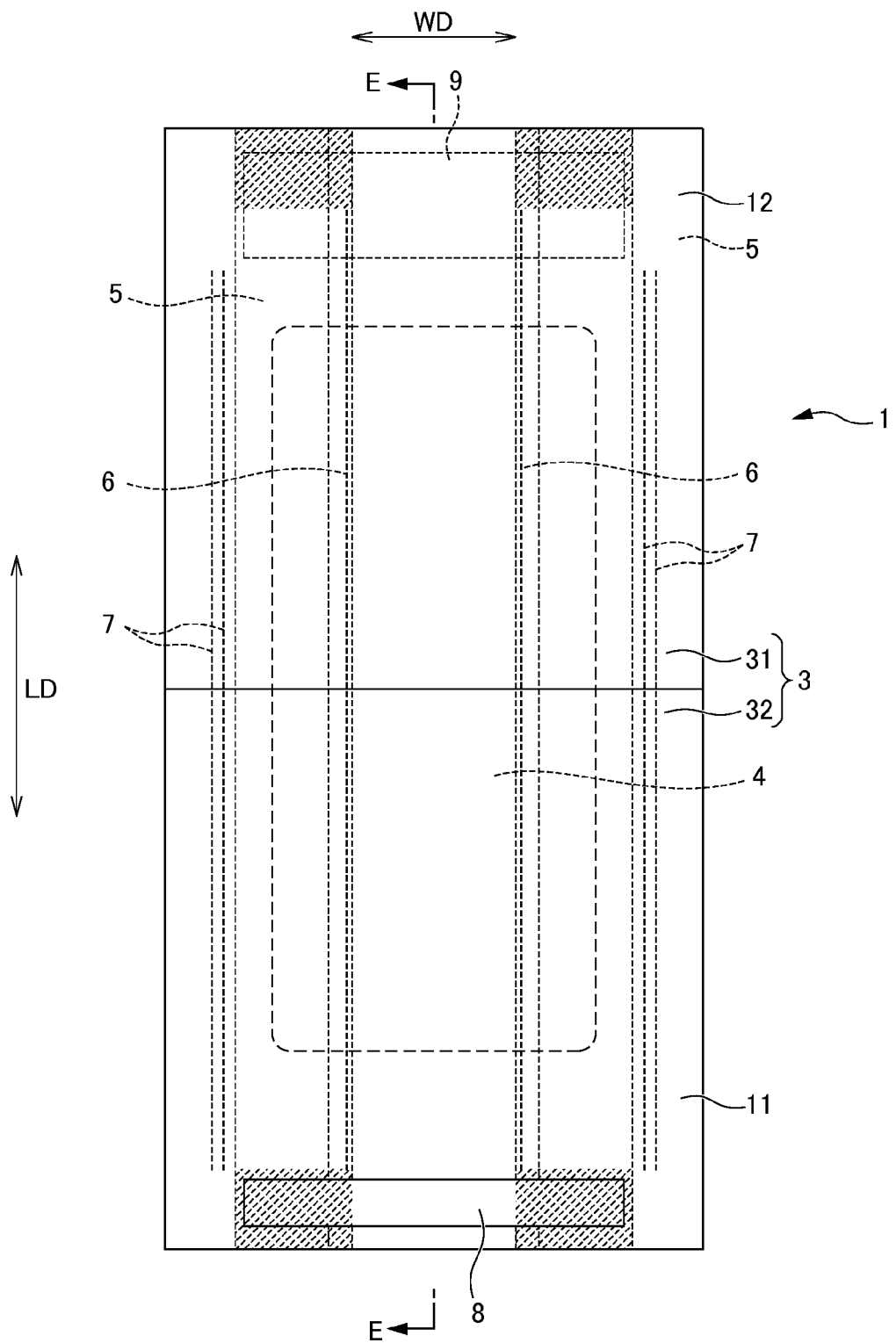
FIG. 11 is a plan view of an absorbent article for pets of a second embodiment viewed from a back surface layer side.
Figure 12:
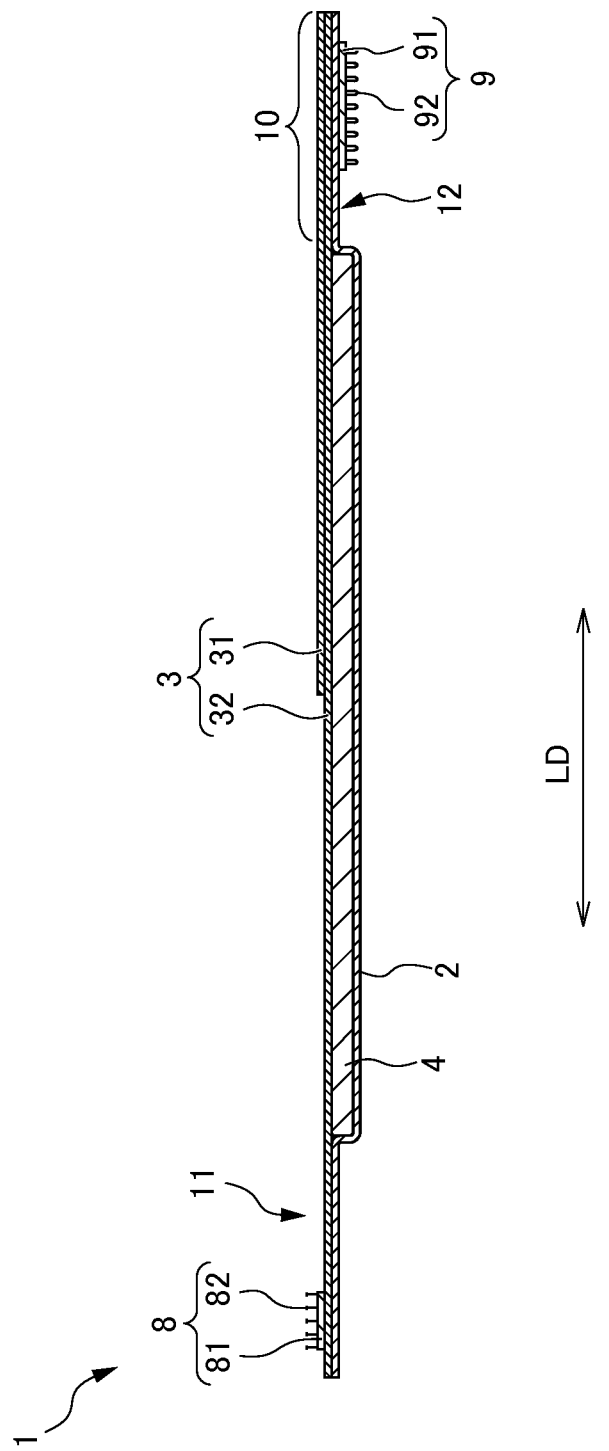
FIG. 12 is a cross-sectional view taken along the E-E line of FIG. 11.

The absorbent article 1 for pets according to a second embodiment of the present invention will now be described with reference to FIGS. 11 and 12. FIG. 11 is a plan view of the absorbent article 1 for pets according to the second embodiment, viewed from the back surface layer 3 side. FIG. 12 is a cross-sectional view taken along the E-E line of FIG. 11.

It should be noted that same numerals refer to same components in describing the second embodiment, and explanations thereof will be omitted or simplified.

The absorbent article 1 for pets according to the second embodiment differs from the first embodiment primarily in the configurations of an engaging section and the back surface layer 3.

Specifically, as shown in FIGS. 11 and 12, in the second embodiment, the engaging section is configured by a loop member 9 disposed on the top sheet 2 side of the second end portion 12. As shown in FIG. 12, the loop member 9 has a belt-like configuration and is disposed so that the longitudinal direction thereof is in line with the width direction WD of the absorbent article 1 for pets.

The loop member 9 includes a belt-like base portion 91 and a plurality of loop portions 92 disposed on one face of a base 91. The loop member 9 is attached to the top sheet 2 and the side sheets 5, 5 so that its face having the plurality of loops 92 becomes an inner face of the absorptive article 1 for pets.

The base portion 91 and a plurality of the loop portions 92 of the loop member 9 are integrally formed by using a synthetic resin material such as polyester or the like.

Furthermore, in the second embodiment, the back surface sheet 31 is disposed only in the region from the center in the longitudinal direction LD to the second end portion 12 of the absorbent article 1 for pets. Thus, an outer face side of the absorbent article 1 for pets is entirely covered with the wet-proof sheet 32, and the back surface sheet 31 covers a half region of this wet-proof sheet 32 in the vicinity of the second end portion 12.

In accordance with the absorbent article 1 for pets of the second embodiment, in addition to the above-mentioned operational effects (1) to (3), the following operational effects are obtained.

(5) When the absorbent article 1 for pets is folded in two in the longitudinal direction LD, the weak engagement section 10 cannot be formed in the vicinity of the first end portion 11. Thus, the back surface sheet 31, which is disposed on an outer face side of the back surface layer 3, was disposed in a region from the center in the longitudinal direction LD to the second end portion 12 of the absorbent article 1 for pets. This allows reduction of the quantity of the back surface sheet 31 used while enabling stable packaging of the stacked plurality of the absorbent articles 1 for pets in the bag 20.

Figure 13:
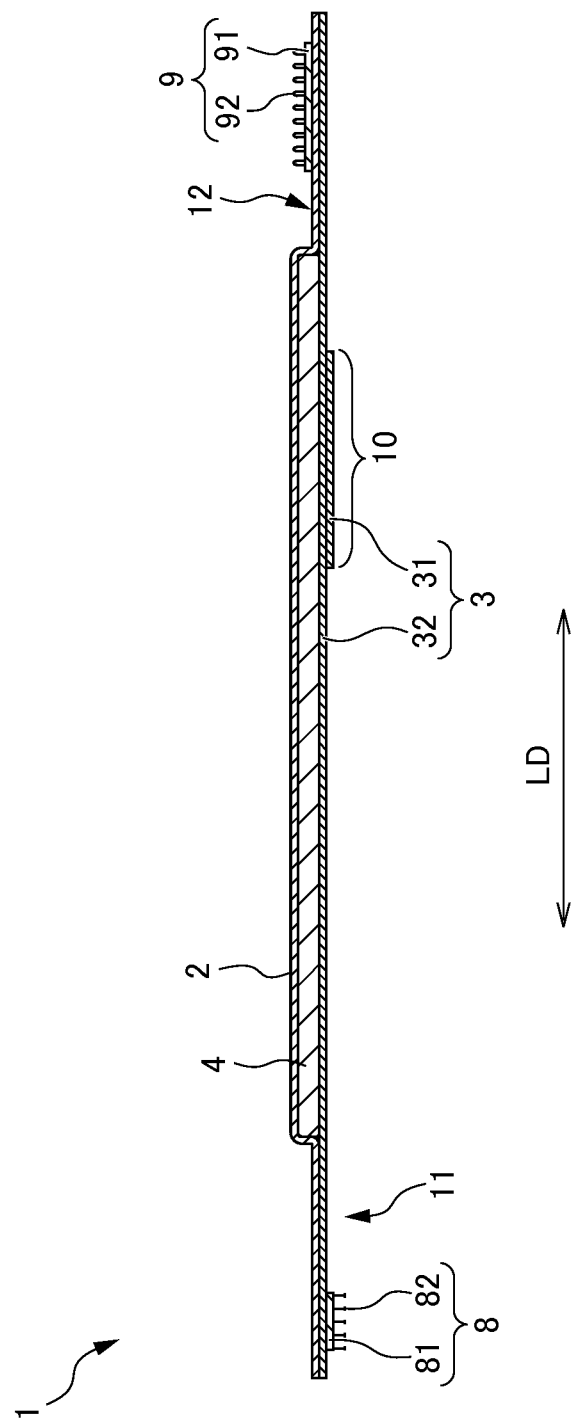
FIG. 13 is a longitudinal cross-sectional view of an absorbent article for pets of a third embodiment, corresponding to FIG. 12.
Figure 14:
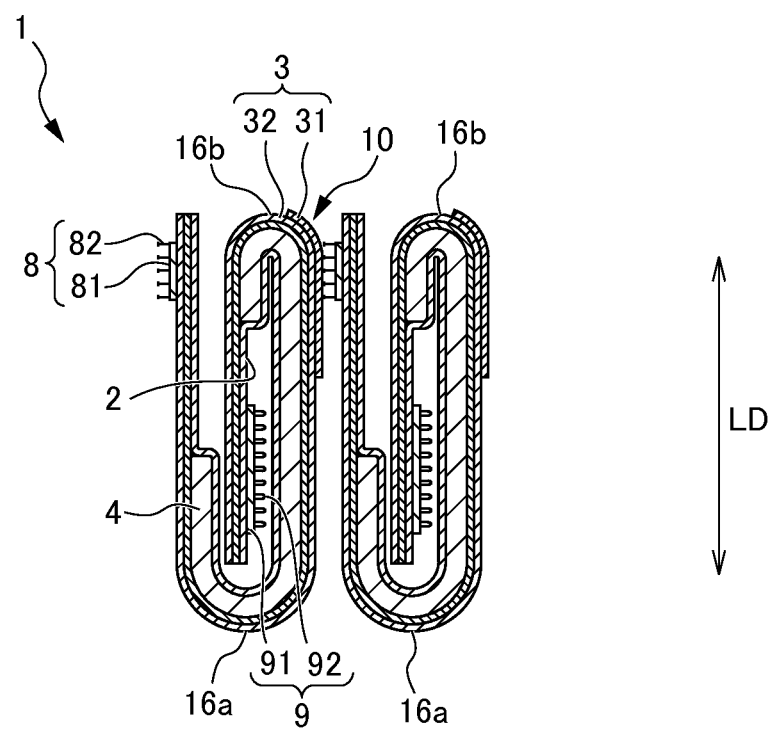
FIG. 14 shows the absorbent articles for pets of the third embodiment in a state folded in three and stacked.

The absorbent article 1 for pets according to a third embodiment of the present invention will now be described with reference to FIGS. 13 and 14. FIG. 13 is a longitudinal cross-sectional view of the absorbent article 1 for pets according to the third embodiment, corresponding to FIG. 12. FIG. 14 shows the absorbent articles for pets of the third embodiment in a state folded in three and stacked.

The absorbent article 1 for pets of the third embodiment differs from the second embodiment primarily in the configuration of the back surface layer 3.

In the absorbent article 1 for pets of the third embodiment, as shown in FIGS. 13 and 14, the back surface sheet 31 is exclusively positioned in a region in the vicinity of either a bending portion 16a or 16b located on the second end portion 12 side, which the bending portions 16a, 16b are formed where the absorbent article 1 for pets is folded in three in the longitudinal direction LD.

As shown in FIG. 14, the absorbent article 1 for pets of the third embodiment is packaged in the bag 20 where a plurality thereof are respectively folded in three and stacked. Here, in the third embodiment, the back surface sheet 31 is positioned in a region in the vicinity of the bending portion 16b located on the second end portion 12 side, which the bending portion 16b as well as the bending portion 16a is formed when the absorbent article 1 for pets is folded in three in the longitudinal direction LD. Thus, when a plurality of absorbent articles 1 for pets is stacked, the hook tape 8 of one absorbent article 1 for pets contacts adjacently disposed the absorbent article 1 for pets in the region where the back surface sheet 31 is disposed, thereby weakly engaging with this back surface sheet 31.

In accordance with the absorbent article 1 for pets of the third embodiment, in addition to the above-mentioned operational effects (1) to (3), the following operational effects are obtained.

(6) The back surface sheet 31 was disposed in a region in the vicinity of the bending portion 16b located on the second end portion 12 side, which the bending portion 16b as well as the bending portion 16a is formed when the absorbent article 1 for pets is folded in three in the longitudinal direction LD. Consequently, when a plurality of absorbent articles 1 for pets is respectively folded in three and stacked, the hook tape 8 of one absorbent article 1 for pets can contact adjacently disposed the absorbent article 1 for pets by the region where the back surface sheet 31 is disposed, thereby weakly engaging with the back surface sheet 31. This allows reduction of the quantity consumed of the back surface sheet 31 which forms the weak engagement section 10, while enabling secure packaging of a plurality of the absorbent articles 1 for pets, respectively folded in three and stacked together, in the bag 20.

The present invention has been described hitherto through the preferable embodiments, which do not limit the scope of the invention; suitable modifications may be practiced.

For example, the present invention is not limited to the two-layer configuration of the back surface layer 3 with the back surface sheet 31 and the wet-proof sheet 32 in the first and second embodiments. Thus, a back surface layer may be configured only by a back surface sheet made of nonwoven fabric. Or, a back surface layer may be configured by a back surface sheet and a loop member disposed at an engagement section for a hook tape on an outer face of the back surface sheet. Furthermore, a back surface layer may be constituted of a wet-proof sheet and a loop member disposed at an engagement section for a hook tape on an outer face of the back surface sheet.

Furthermore, the present invention is not limited to the longitudinal double-folding or tri-folding of the absorbent article 1 for pets for packaging in the bag 20, as shown in the above embodiments. Thus, an absorbent article for pets may be packaged in a state where it is folded in four in the longitudinal direction.

The invention claimed is:

1. A package of absorbent article for pets, said package comprising:
 a plurality of absorbent articles disposed in a stack, wherein each of the plurality of absorbent article includes:
  a liquid-permeable top sheet;
  a liquid-impermeable back surface layer;
  an absorbent core sandwiched between the top sheet and the back surface layer;
  a first end portion and a second end portion opposite each other in a longitudinal direction of the absorbent article;
  a pair of side portions opposite each other in a width direction of the absorbent article, and connecting the first end portion and the second end portion,
  an elongated hook member disposed on the back surface layer in a vicinity of the first end portion, wherein the elongated hook member has a longitudinal direction extending along an edge of the absorbent article in the width direction;
  an engaging section disposed on the top sheet in a vicinity of the second end portion and engageable with the hook member; and
  a weak engagement section disposed on the back surface layer at a position in contact with the hook member of an adjacent absorbent article in the stack, wherein
   an engagement force between the hook member and the weak engagement section is weaker than an engagement force between the hook member and the engaging section,
   the back surface layer includes a nonwoven fabric engageable with the hook member,
   the hook member is configured to be engaged with the engaging section when the absorbent article is worn, and
   the hook member is engaged with the weak engagement section of the adjacent absorbent article in the stack of the absorbent articles such that the plurality of absorbent articles are engaged with one another to form a stacked body.

2. The package according to claim 1, wherein
 each of the absorbent articles is longitudinally folded in two to form (i) a first outer face defined by the back surface layer in the vicinity of the first end portion and (ii) a second outer face defined by the back surface layer in the vicinity of the second end portion,
 the weak engagement section is provided on the second outer face, and
 the first outer face of one of the absorbent articles in the stack abuts against the second outer face of the adjacent absorbent article in the stack, to bring the hook member of said one of the absorbent articles into engagement with the weak engagement section of the adjacent absorbent article.

3. The package according to claim 1, wherein
 the top sheet includes a nonwoven fabric engageable with the hook member,
 the engaging section is formed by the top sheet, and
 the nonwoven fabric of the back surface layer defines the weak engagement section.

4. The package according to claim 1, wherein the engagement force between the hook member of one of the absorbent articles in the stack and the weak engagement section of the adjacent absorbent article in the stack is lower than the engagement force between the hook member and the engaging section of said one of the absorbent articles when the absorbent article is worn.

* * * * *